(12) United States Patent
Okanda et al.

(10) Patent No.: US 6,807,251 B2
(45) Date of Patent: Oct. 19, 2004

(54) X-RAY DIFFRACTION APPARATUS (75) Inventors: Hitoshi Okanda, Hachioji (JP); Go Fujinawa, Hamura (JP)

(73) Assignee: Rigaku Corporation, Tokyo (JP)

( * ) Notice: Subject to any disclaimer, the term of this patent is extended or adjusted under 35 U.S.C. 154(b) by 115 days.

(21) Appl. No.: 10/328,305

(22) Filed: Dec. 23, 2002

(65) Prior Publication Data
US 2003/0123610 A1 Jul. 3, 2003

(30) Foreign Application Priority Data

Dec. 28, 2001 (JP) ........................................ 2001-400050

(51) Int. Cl.[7] .............................................. G01N 23/20
(52) U.S. Cl. ........................................... 378/71; 378/84
(58) Field of Search ............................ 378/70–85, 147, 378/148

(56) References Cited

U.S. PATENT DOCUMENTS

| | | | | |
|---|---|---|---|---|
| 6,359,964 B1 | * | 3/2002 | Kogan ........................... | 378/87 |
| 6,504,900 B2 | * | 1/2003 | Kondo et al. .................. | 378/70 |
| 6,665,372 B2 | * | 12/2003 | Bahr et al. ..................... | 378/71 |

FOREIGN PATENT DOCUMENTS

| | | |
|---|---|---|
| JP | 09-229879 | 9/1997 |
| JP | 11-072595 | 3/1999 |
| JP | 11-287773 | 10/1999 |
| WO | 00/31523 A | 6/2000 |

OTHER PUBLICATIONS

Z. Barnea et al: "On The Design of a High–Speed Combined High–Resolution Powder Diffractometer and Small–Angle Scattering System With Time–Resolution Capability Based on the Use of Imaging Plates and CCCC Monochromators", Review of Scientific Instruments, American Institute of Physics, New York, U.S., vol. 60, No. 7, Part 2B, Jul. 1, 1989, pp. 2537–2540, XP000038425, ISSN: 0034–6748, "p. 2539, right–hand column; Figure 1.

* cited by examiner

*Primary Examiner*—Craig E. Church
*Assistant Examiner*—Jurie Yun
(74) *Attorney, Agent, or Firm*—Frishauf, Holtz, Goodman & Chick, P.C.

(57) ABSTRACT

In the measurement with the focusing method, an X-ray beam from an X-ray source passes through an opening of a path-selection slit device and is narrowed by a divergence slit with a predetermined divergence angle and is thereafter incident upon a sample. The changing operation from the focusing method into the parallel beam method is carried out by turning, by 180 degrees, the path-selection slit device around its axis of rotation and by moving the divergence slit in a direction perpendicular to an X-ray traveling direction. Then, the X-ray beam from the X-ray source is reflected by a multilayer mirror to become a parallel beam and passes through the opening of the path-selection slit device and is thereafter incident upon the sample. Thus, the turning of the path-selection slit device enables the change between the focusing method and the parallel beam method, requiring no re-setting operation for the optical system.

7 Claims, 7 Drawing Sheets

X-RAY DIFFRACTION APPARATUS

BACKGROUND OF THE INVENTION

This invention relates to X-ray diffraction apparatus in which the focusing method and the parallel beam method can be changed for each other.

X-ray diffraction apparatus may be classified to, in view of X-ray beam divergency, the focusing method and the parallel beam method. In the focusing method, an X-ray beam from an X-ray source is a divergent beam with a predetermined divergence angle and incident upon a sample with a wide irradiation area. Then, the X-ray beam is diffracted by the sample, focused on a receiving slit and thereafter detected by an X-ray detector. In the parallel beam method, on the other hand, an X-ray beam from an X-ray source is made parallel with the use of collimating means, for example a Soller slit or a monochromator, and incident upon a sample. Then, the X-ray beam is diffracted by the sample with keeping the parallel characteristic and is detected by an X-ray detector.

X-ray diffraction apparatus belonging to the focusing method and other X-ray diffraction apparatus belonging to the parallel beam method are usually different from each other. If there is required both of the measurements with the focusing method and with the parallel beam method, the two kinds of the X-ray diffraction apparatus must be prepared. Alternatively, one set of X-ray diffraction apparatus may be used selectively for the focusing method or for the parallel beam method, provided that an exchange of an optical system is required. For example, assuming that a parabolic multilayer mirror is used for making a parallel beam, the focusing method can be changed for the parallel beam method as described below. In the focusing method, an X-ray incident path from an X-ray source to a sample is straight. The change from the focusing method to the parallel beam method requires insertion of the multilayer mirror into the straight incident path. Sine the insertion of the multilayer mirror causes a bend of the X-ray beam path, the sample position must be changed if the X-ray source remains at the same position. Alternatively, the X-ray source position must be changed if the sample remains at the same position. Besides, with the change of the incident optical system, the setting operation for the optical system, i.e., adjustment of the optical axis, must be carried out again.

Then, for obviating the above problems, improved X-ray diffraction apparatus has been developed in which the focusing method and the parallel beam method can be changed for each other substantially without the change of the positional relationship between the X-ray source and the sample. X-ray diffraction apparatus disclosed in Japanese patent publication 9-229879 A (1997) can obtain an X-ray beam for the focusing beam and also an X-ray beam for the parallel beam method with the use of an improved slit device. Other X-ray diffraction apparatus disclosed in Japanese patent publication 11-72595 A (1999) can obtain an X-ray beam for the focusing beam and also an X-ray beam for the parallel beam method with the change between the vertical and horizontal arrangements of a curved-crystal monochromator, noting that the monochromator is used for both of the focusing method and the parallel beam method.

Since the apparatus in Japanese patent publication 9-229879 A (1997) mentioned above obtains the parallel beam by narrowing the opening widths of a plurality of slit devices, there is the problem that the X-ray intensity on the sample becomes weaker in using the parallel beam method. Of course, the apparatus can not use a parabolic multilayer mirror which is superior for making the parallel beam. On the other hand, since the other apparatus disclosed in Japanese patent publication 11-72595 A (1999) mentioned above changes the posture of a curved-crystal monochromator for carrying out the change between the focusing method and the parallel beam method, the setting operation for the optical system is required again. Besides, since the apparatus makes the parallel beam with the curved-crystal monochromator which is in the vertical arrangement, the intensity of the obtained parallel is not sufficient. At any rate, the apparatus also can not use the parabolic multilayer mirror.

SUMMARY OF THE INVENTION

It is an object of the present invention to provide X-ray diffraction apparatus which can conduct easy change between the focusing method and the parallel beam method.

It is another object of the present invention to provide X-ray diffraction apparatus which can use, in the parallel beam method, a parabolic multilayer mirror to obtain a sufficient intensity of X-rays with a high resolution.

X-ray diffraction apparatus according to the present invention is for the apparatus in which an X-ray source emits an X-ray beam which is incident upon a sample, diffracted by the sample and detected by an X-ray detector. The X-ray diffraction apparatus comprises: (a) a first incident path along which the X-ray beam is incident upon the sample with a predetermined divergence angle; (b) a second incident path along which the X-ray beam is reflected by a parabolic multilayer mirror to become a parallel beam and thereafter incident upon the sample; (c) a path-selection slit device which can open any one of the first incident path and the second incident path whereas close off the other of the first incident path and the second incident path; (d) an X-ray source in which a position of X-ray generation does not vary independently upon the selection of the first incident path or the second incident path; and (e) a sample holder in which a center position of the sample does not vary independently upon the selection of the first incident path or the second incident path.

The first incident path corresponds to a path for the focusing method, whereas the second incident path corresponds to a path for the parallel beam method. With the present invention, the first and the second incident paths can be selectively changed between the opened and closed off conditions with the use of the path-selection slit device, so that the focusing method and the parallel beam method can be easily changed for each other, requiring no re-setting operation for the optical system. Besides, since the parallel beam method uses the parabolic multilayer mirror, the obtained parallel beam has a good monochromatic property, i.e., a high resolution, and a high intensity as compared with the conventional X-ray diffraction apparatus enabling the change between the focusing method and the parallel beam method.

The X-ray diffraction apparatus according to the present invention may be used in a manner that, for example, the measurement placing priority on the X-ray diffraction intensity can be carried out with the focusing method which uses a direct beam, whereas the precise measurement placing priority on the angular resolution can be carried out with the parallel beam method which uses the parabolic multilayer mirror.

Since the parabolic multilayer mirror has a reflection surface which is made of a synthetic multilayer thin film, the mirror can be synthetically processed to have a small diffraction angle, about several degrees. If the diffraction angle of the mirror is small, the angle formed by the first incident path and the second incident path becomes small advantageously. As a result, the X-ray tube may be kept stationary with the same posture with no problem although the X-ray take-off direction differs between the two incident paths.

DETAILED DESCRIPTION OF THE PREFERRED EMBODIMENTS

Figure 1:
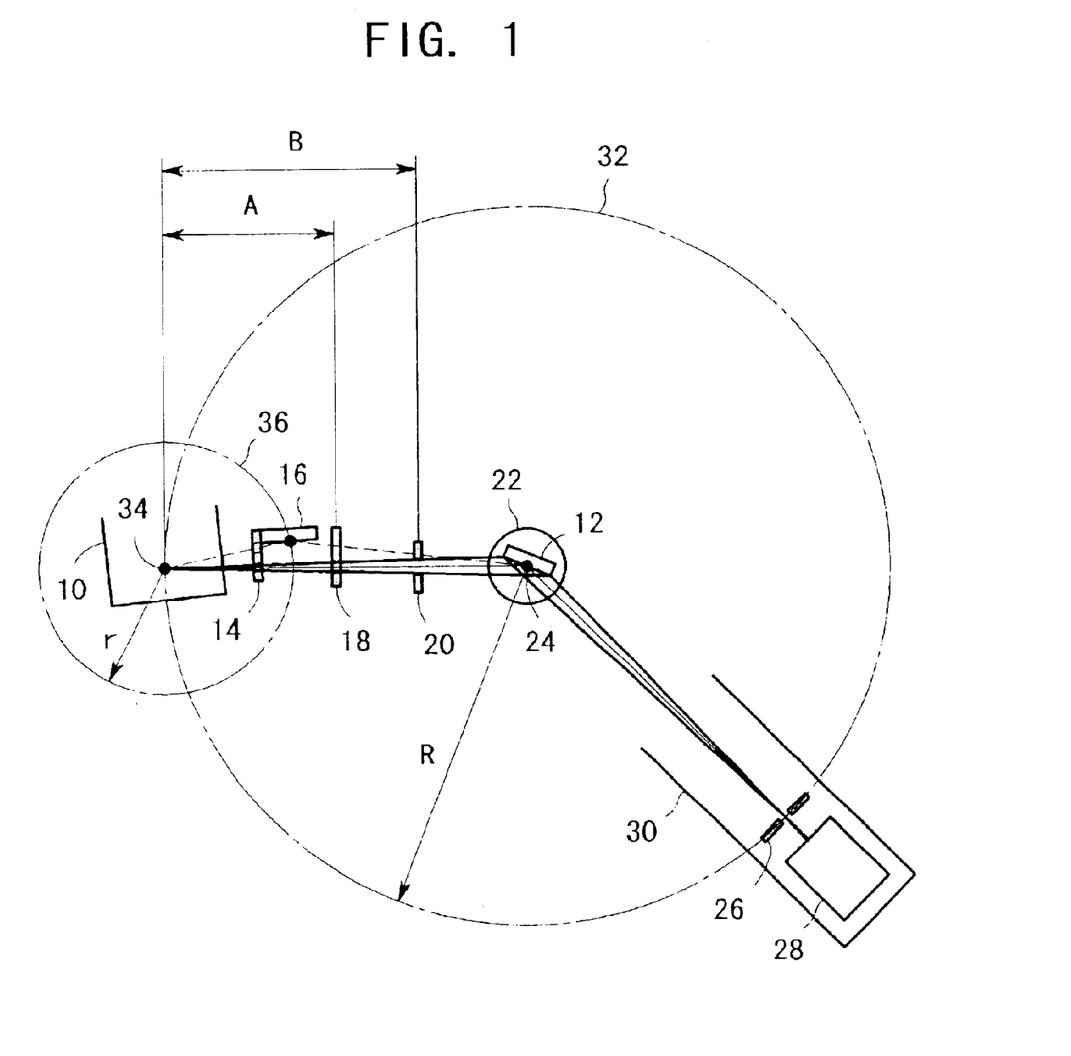
FIG. 1 is a plan view illustrating the elementary configuration of the first embodiment of X-ray diffraction apparatus according to the present invention.

Referring to FIG. 1 showing the first embodiment, X-ray diffraction apparatus has an X-ray tube 10 and a sample 12 between which there are arranged an aperture slit plate 14, a multilayer mirror 16, a path-selection slit device 18 and a divergence slit 20 in the described order from the X-ray tube 10 side. The sample 12 rests on a sample holder 22 which can rotate around an axis of rotation 24 of a goniometer. A receiving slit 26 and an X-ray detector 28 rest on a detector support 30 which also can rotate around the axis of ration 24 of the goniometer. The goniometer has a turning radius R of 285 mm, i.e., a radius of the focusing circle 32, the receiving slit 26 and the X-ray focus 34 being disposed on the focusing circle 32. The X-ray focus 34 has an electron-beam-irradiation region on a target with a size of 1 mm×10 mm for example. The X-ray focus extends longitudinally in a direction perpendicular to the drawing sheet of FIG. 1.

The multilayer mirror 16 has a longitudinal center disposed on a circle 36 having a radius r, 100 mm, whose center is on the X-ray focus 34. The distance A between the X-ray focus 34 and the path-selection slit device 18 is 135 mm, and the distance B between the X-ray focus 34 and the divergence slit 20 is 200 mm.

Figure 2A:
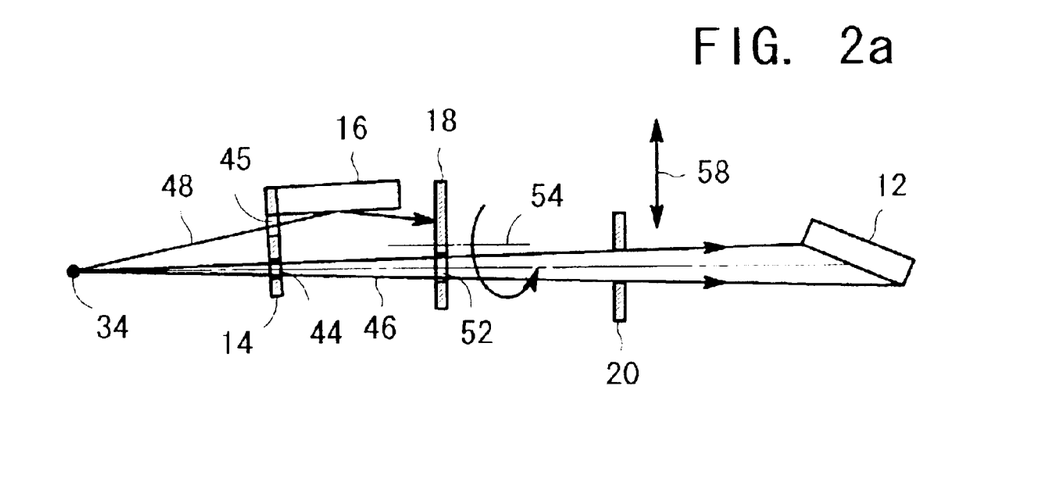
FIGS. 2a, 2b and 2c are enlarged plan views illustrating three different conditions of the incident optical system of the X-ray diffraction apparatus shown in FIG. 1.
Figure 2B:
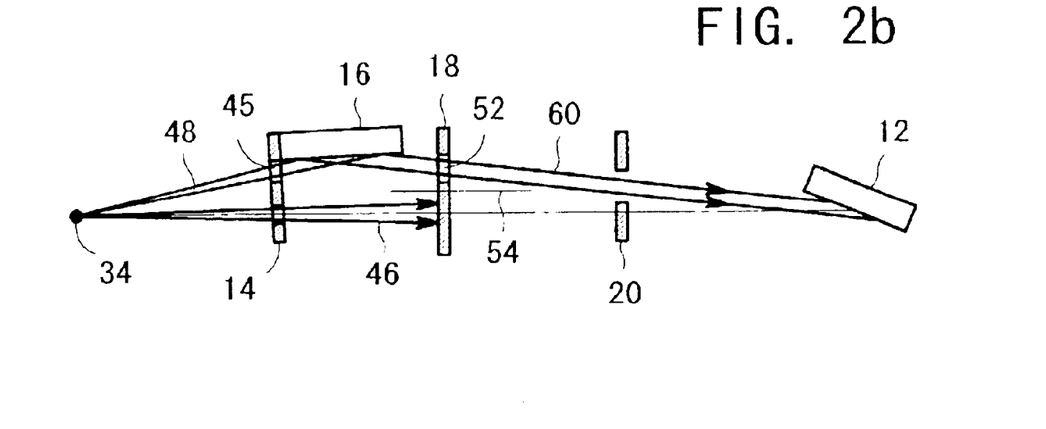

FIG. 2a shows the first incident path for the focusing method, whereas FIG. 2b shows the second incident path for the parallel beam path. Referring to FIG. 2a, a part of the X-rays emitted from the X-ray focus 34 passes through the first aperture 44 of the aperture slit plate 14, passes through an opening 52 of the path-selection slit device 18, passes through the divergence slit 20 to be narrowed to a predetermined divergence angle, and thereafter is incident upon the sample 12.

Figure 3:
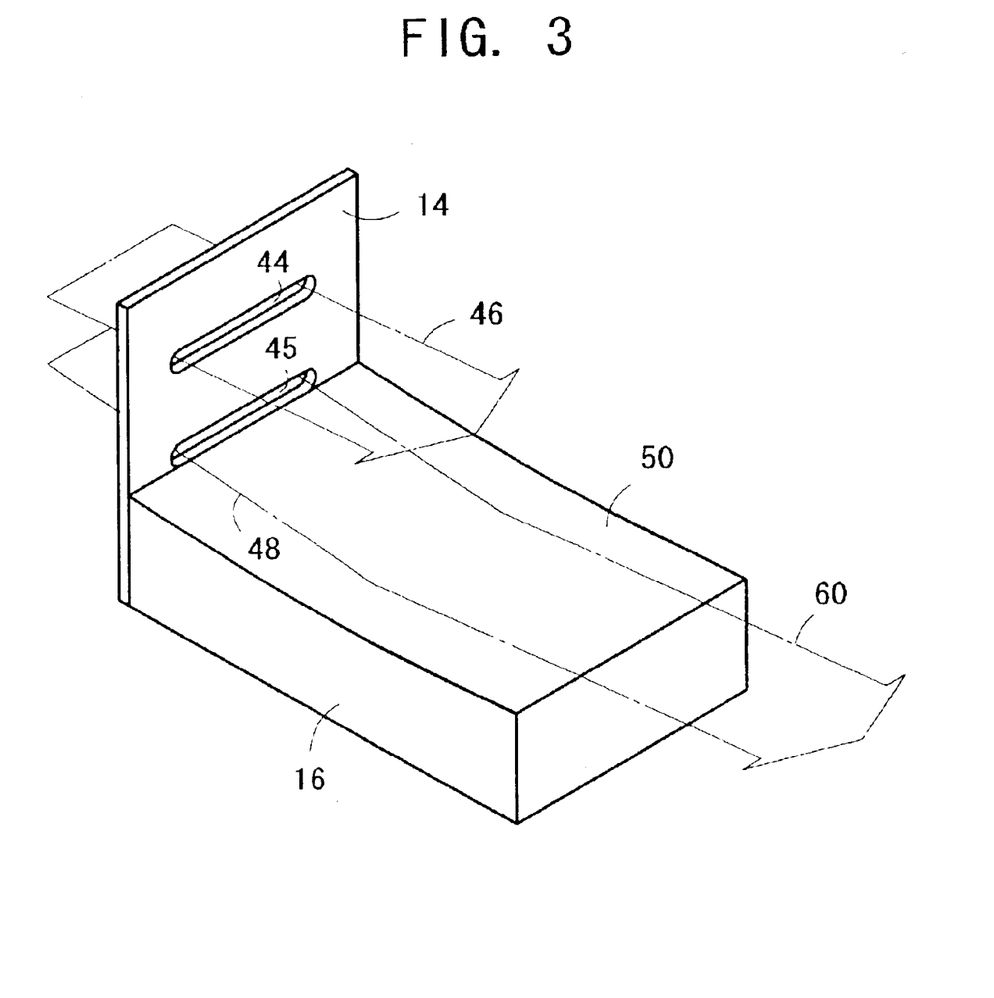
FIG. 3 is a perspective view illustrating an aperture slit plate and a parabolic multilayer mirror.

Referring to FIG. 3, the aperture slit plate 14 is fixed, by screw means, to an end face of the multilayer mirror 16 to become a united assembly. The aperture slit plate 14 is formed with the first aperture 44 and the second aperture 45.

The X-ray beam 46 passing through the first aperture 44 will travel for the sample, whereas the X-ray beam 48 passing through the second aperture 45 is reflected by the reflection surface 50 of the mirror 16 to become a parallel beam 60 and then will travel for the sample. The two apertures 44 and 45 have the same size, 0.9 mm in width and about 13 mm in length.

The reflection surface 50 of the multilayer mirror 16 has a parabolic surface, the mirror 16 being so disposed that the X-ray focus is on the focal point of the parabolic surface. Accordingly, the X-ray beam reflected by the reflection surface 50 would become a parallel beam. The reflection surface 50 is made of a synthetic multilayer thin film in which a heavy element and a light element are alternately layered. The multilayer period of the multilayer thin film varies continuously along the parabolic surface, so that X-rays having a certain wavelength, $CuK\alpha$ rays in this embodiment, can satisfy the Bragg's diffraction condition at every points on the reflection surface. The parabolic multilayer mirror of this type is disclosed in Japanese patent publication 11-287773 A (1999) for example. Since the mirror 16 can reflect selectively only X-rays having a certain wavelength to make a parallel beam, it can be said that the mirror is a monochromator.

Figure 4A:
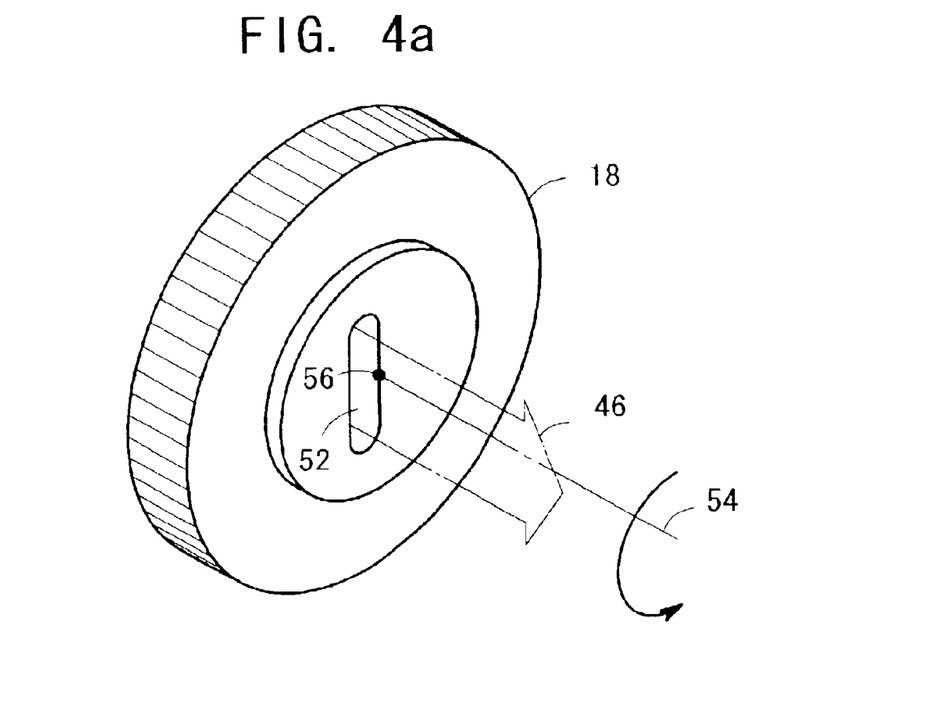
FIGS. 4a and 4b are perspective views illustrating two different conditions of a path-selection slit device.
Figure 4B:
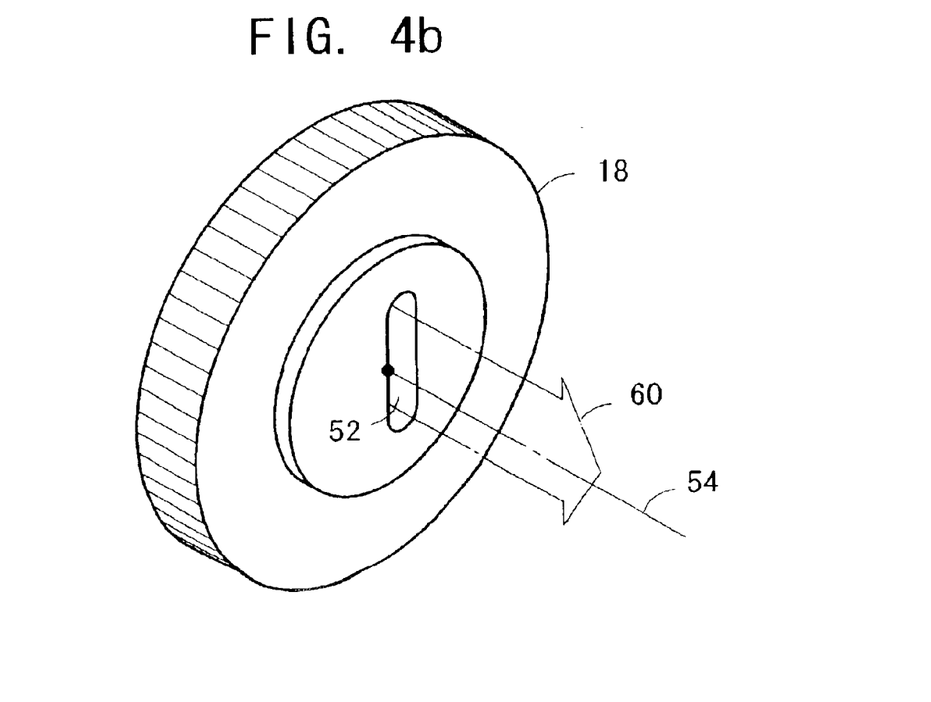

Referring to FIG. 4a, the path-selection slit device 18 has a substantially disc-like appearance and has an elongate opening 52 near its center. The opening 52 is 3 mm in width and about 12 mm in length. The path-selection slit device 18 can turn by 180 degrees around the axis of rotation 54. The opening 52 is so formed as to be eccentric with respect to the center 56 of the path-selection slit device 18. In the illustrated condition in FIG. 4a, the opening 52 is positioned at the left side of the axis of rotation 54. Turing the path-selection slit device 18 by 180 degrees around the axis of rotation 54, it becomes the condition shown in FIG. 4b, the opening 52 being positioned at the right side of the axis of rotation 54. The path-selection slit device 18 in the condition in FIG. 4a allows only the X-ray beam 46 for the focusing method to pass through the opening 52, whereas the path-selection slit device 18 in the condition in FIG. 4b allows only the X-ray beam 60 for the parallel beam method, i.e., the parallel beam having been reflected by the mirror, to pass through the opening 52.

Referring to FIG. 2a again, the divergence slit 20 has an opening width which can be regulated with the use of an electric motor, and the slit 20 is movable in a direction 58 perpendicular to the X-ray travelling direction.

Next, there will be explained how to use the X-ray diffraction apparatus. First, the setting operation of the incident optical system will be explained. Referring to FIG. 1, the X-ray tube 10 and the multilayer mirror 16 rest on the common adjusting base which is not shown. The mirror 16 and the X-ray tube 10 have been positioned to satisfy the theoretical, positional relationship. First of all, the path-selection slit device 18 is set at the turning position at which the X-ray beam for the parallel beam method passes through. Under the condition, the X-ray beam which has reflected by the mirror 16 passes through the path-selection slit device 18. Next, the mirror 16 is rotated within a range of small angle around its center, i.e., around an axis of rotation which is perpendicular to the drawing sheet of FIG. 1, and the X-ray intensity of the parallel beam is detected by the X-ray detector 28 which should be moved to the angular position at which the parallel beam can be detected. Then, the rotational position of the mirror 16 is adjusted so as to give the maximum X-ray intensity, completing the precise determination of the positional relationship between the X-ray tube 10 and the mirror 16. Next, the adjusting base mentioned above is moved slightly in a direction up and down in FIG. 1 so that the parallel beam passes through precisely the axis of rotation 24 of the goniometer, completing the setting operation of the incident optical system for the parallel beam method.

Next, the path-selection slit device 18 is set at the other turning position at which the X-ray beam of the focusing method passes through. Then, the divergence slit 20 is moved slightly in a direction perpendicular to the X-ray beam path, i.e., in a direction up and down in FIG. 1, so that the X-ray tube 10, the divergence slit 20 and the axis of rotational 24 can be on a straight line under the condition that the opening width of the divergence slit 20 is extremely narrowed. Now, the setting operation for the incident optical system in the focusing method has been completed too.

Next, there will be explained the X-ray diffraction measurement using the focusing method. With the condition shown in FIG. 2a, the X-ray diffraction measurement for the sample 12 can be carried out with the use of the focusing method. The path-selection slit device 18 is under the condition shown in FIG. 4a and only the X-ray beam 46 for the focusing method can pass through the opening 52 of the path-selection slit device 18. The X-ray beam 46 is narrowed to a predetermined divergence angle by the divergence slit 20 and incident upon the surface of the sample 12. Assuming that the divergence slit 20 is positioned at a distance of 200 mm from the X-ray focus 34 and the opening width is 1.75 mm for example, the divergence angle of the X-ray beam becomes 0.5 degrees. The two slit blades which define the opening width of the divergence slit 20 can be opened and closed transversely and symmetrically under the control of the electric motor. Since the width of the opening 52 of the path-selection slit device 18 is 3 mm as wide, the X-ray beam 46 which will be narrowed by the divergence slit 20 is not interfered with the opening 52 of the path-selection slit device 18 even when the divergence slit 20 is set to have the maximum divergence angle, 2 degrees for example. On the other hand, the width of the first aperture 44 of the aperture slit plate 14 is 0.9 mm which is comparatively narrow. But, since the aperture slit plate 14 is positioned near the X-ray focus 34, 80 mm from the X-ray focus 34, the X-ray beam 46 which will be narrowed by the divergence slit 20 is not interfered with the aperture slit plate 14 either.

It is noted that the X-ray beam 46 having the predetermined divergence angle can be realized only with the divergence slit 20, requiring no aperture slit plate 14. The aperture slit plate 14, however, has a function described below. The aperture slit plate 14 prevents unnecessary X-rays from entering into the incident optical system. That is, only the X-ray beam 46 for the focusing method and the X-ray beam 48 for the parallel beam method can pass through the aperture slit plate 14 and other X-rays can not enter into the incident optical system, reducing the influence of scattered X-rays.

In the condition shown in FIG. 2a, the other X-ray beam 48 passes through the second aperture 45 of the aperture slit plate 14 and is then reflected by the multilayer mirror 16. The parallel beam from the mirror 16 is, however, cut off by the path-selection slit device 18 and does not reach the sample 12.

Referring to FIG. 1 again, in the X-ray diffraction measurement with the focusing method, the receiving slit 26 is used and the diffracted X-rays from the sample 12 is detected by the X-ray detector 28, under the condition that the sample 12 and the detector support 30 are rotated synchronously with an angular velocity ratio of 1 to 2 to obtain an X-ray diffraction pattern.

Next, there will be explained the changing operation from the focusing method shown in FIG. 2a to the parallel beam method shown in FIG. 2b. First, the path-selection slit device 18 is turned by 180 degrees around its axis of rotation 54, the path-selection slit device 18 becoming the condition shown in FIG. 4b. The X-ray beam 48 for the parallel beam method passes, as shown in FIG. 3, through the second aperture 45 of the aperture slit plate 14 and is then reflected by the multilayer mirror 16 to become the parallel beam 60. Only the parallel beam 60 can pass through the opening 52 of the path-selection slit device 18 as shown in FIG. 2b, whereas the X-ray beam 46 for the focusing method is cut off by the path-selection slit device 18. The divergence slit 20 is moved in a direction perpendicular to the X-ray beam travelling direction so that the center of the divergence slit 20 becomes on the center of the parallel beam 60 which comes from the mirror 16. If the use of all the parallel beam 60 is desired, the divergence slit 20 should have the maximum opening width so as not to interfere the parallel beam 60. On the other hand, if the limited beam width is desired, the divergence slit 20 should have the regulated slit width so as to define the desired beam width. Thus, the change from the focusing method to the parallel beam method has been completed, under the condition that both of the position of the X-ray focus 34 and the center position of the sample do not vary and only the path-selection slit device 18 and the divergence slit 20 are moved. A re-setting operation for the optical system is not required. Since the X-ray source, the sample and the multilayer mirror are not moved at all in the change operation from the focusing method and the parallel beam method, the beginning-adjusted setting condition is not losed.

Figure 2C:
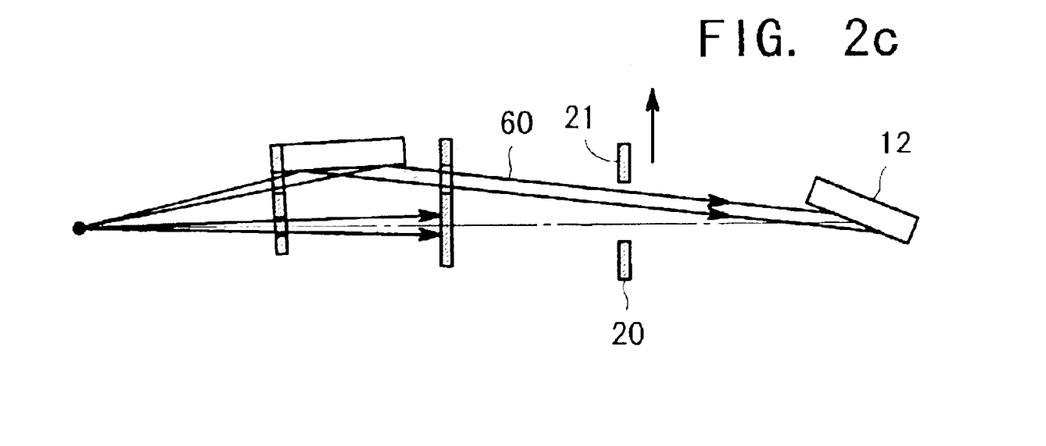

If it is intended not to narrow the beam width of the parallel beam 60 with the divergence slit 20, the divergence slit 20 may not be moved as a whole but only one of the slit blades may be moved. That is, as shown in FIG. 2c, the upper-side-in-drawing slit blade 21 may be moved up in the drawing to widely open the slit, so that the parallel beam 60 would not be interfered with the divergence slit 20.

In the X-ray diffraction measurement with the parallel beam method, the receiving slit 26 shown in FIG. 1 may be removed from the detector support 30, or alternatively the opening width of the receiving slit 26 may be extremely wide. The X-ray detector 38 is preferably moved to the sample 12 to increase the X-ray detection intensity. Therefore, the X-ray detector 38 may be designed so as to slide in the longitudinal direction of the detector support 30.

Figure 7:
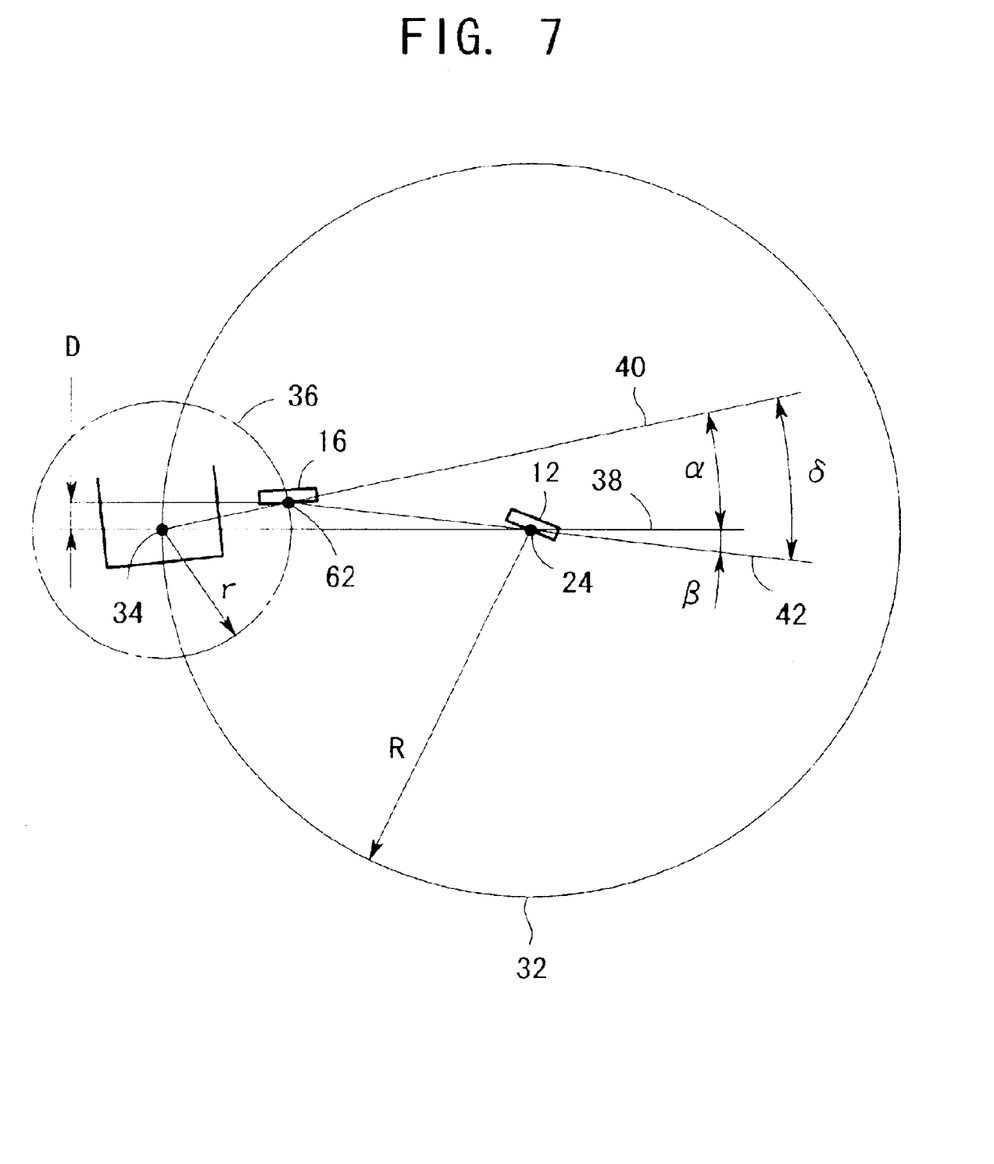
FIG. 7 is a plan view explaining the setting position of the multilayer mirror.

Next, the setting position of the multilayer mirror 16 will be explained in detail. Referring to FIG. 7, the multilayer mirror 16 must be precisely positioned so that the X-ray beam which has been reflected by the mirror 16 can pass through the axis of rotation 24 of the goniometer. If such a requirement is satisfied, the change between the focusing method and the parallel beam method could be realized with no movement of the X-ray focus 34 and no movement of the center of the sample 12. The mirror 16 is designed for CuKα rays and has a parabolic surface whose focal point is at a distance of 100 mm from the longitudinal center 62 of the mirror 16, the longitudinal center 62 being referred to hereafter simply as the center of the mirror 16. Accordingly, the mirror 16 should be positioned so that the center 62 of the mirror 16 can be at the distance of 100 mm from the X-ray focus 34. So long as the center 62 of the mirror 16 is at any point on the circle 36, which has a center at the X-ray focus 34 and has a radius of 100 mm, the mirror 16 could generate the parallel beam.

Next, the distance D shown in FIG. 7 must be determined so that the parallel beam which has been reflected by the mirror 16 can pass through the axis of rotation 24 of the goniometer. The distance D is a distance from the straight line, which connects the X-ray focus 34 and the axis of rotation 24 of the goniometer, to the center 62 of the mirror 16. The distance D can be calculated with the following Equation (1). An angle α will be mentioned later.

$$D = r \sin \alpha \quad (1)$$

The mirror 16 is so designed that the angle δ formed by the incident X-rays and the outgoing X-rays becomes 2.4 degrees. The angle δ is equal to twice the Bragg angle $\theta_M$ with which X-rays can be reflected by the reflection surface of the mirror 16. The mirror 16 is designed for the use of CuKα, whose wavelength is 0.154 nanometers, and the multilayer period of the multilayer thin film is 3.7 nanometers at the center 62 of the mirror 16. The angle α is defined as an angle fromed by the straight line 38 going from the X-ray focus 34 to the center of the sample 12 (i.e., the axis of rotation 24 of the goniometer) and the straight line 40 going from the X-ray focus 34 to the center of the mirror 16. The angle β is defined as an agnle between the straight line 38 mentioned above and the straight line 42 which indicates the travelling direction of the parallel X-ray beam from the mirror 16. The relationship among the angles is represented by the following Equation (2).

$$\alpha + \beta = \delta = 2\theta_M \quad (2)$$

Imagining a triangle having three vertices on the X-ray focus 34, the center 62 of the mirror 16 and the axis of rotation 24 of the goniometer, the angles β and δ satisfy the following Equation (3).

$$\sin \beta = (r/R) \sin \delta \quad (3)$$

In Equation (3), since δ (=2.4 degrees), R (=285 mm) and r (=100 mm) are known, the angle β can be calculated to be 0.84 degrees. This measure of β is assigned in Equation (2), so that α becomes 1.56 degrees. Therefore, from Equation (1), the distance D (=r·sin α) becomes 2.7 mm. Thus, the position of the mirror 16 has been determined. Under this condition, the parallel beam which has been reflected by the mirror 16 would pass through the axis of rotation 24 of the goniometer.

Although the measure of D, 2.7 mm, is very small as compared with the measures of R and r, it should be noted that the distance D is exaggerated in FIGS. 1, 2 and 7 for easy understanding.

The angle formed by the direction in which the X-ray beam for the focusing method goes out from the X-ray focus and the direction in which the X-ray beam for the parallel beam method goes out from the X-ray focus is equal to the angle α mentioned above and is 1.56 degrees. Since the measure of angle α is much smaller than the X-ray take-off angle, usually 6 degrees, at the target surface of the X-ray tube, it would cause no problem that the X-ray tube is kept stationary perfectly in changing the focusing method for the parallel beam method. That is, if the X-ray take-off angle is assumed to be 6 degrees in the focusing method, the X-ray take-off angle would become 4.44 or 7.56 degrees in the parallel beam method.

Figure 6A:
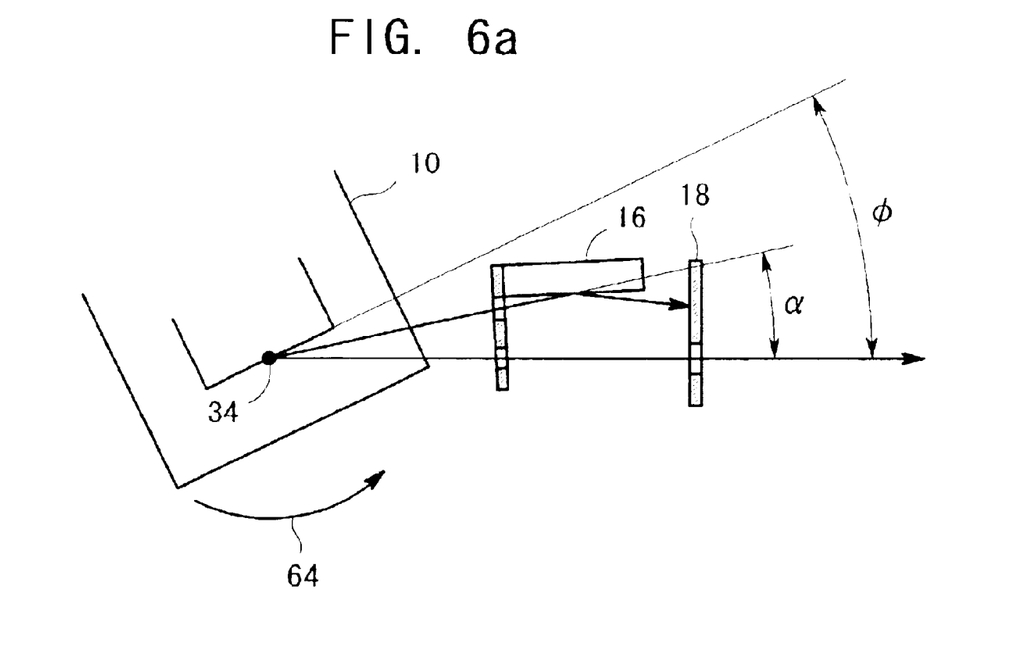
FIGS. 6a and 6b are plan views explaining a movement of the X-ray tube in the second embodiment of the X-ray diffraction apparatus according to the present invention.
Figure 6B:
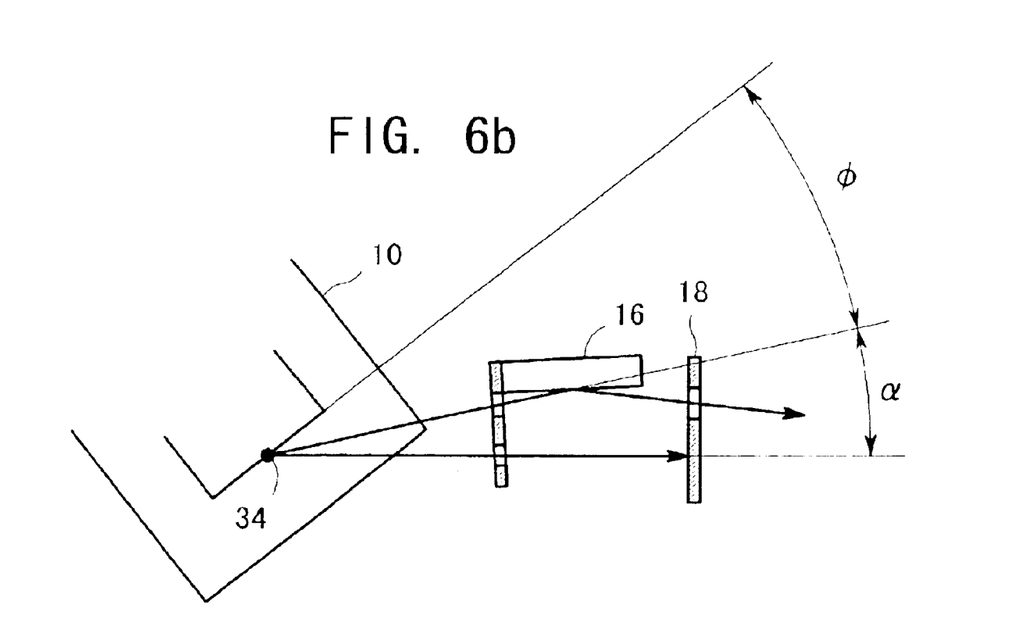

FIG. 6 shows the movement of an X-ray tube in the second embodiment of the X-ray diffraction apparatus according to the invention. In the second embodiment, the X-ray tube 10 can be slightly turned around the X-ray focus 34, other structures being the same as that in the first embodiment. The second embodiment would be effective for the case that the angle α formed by the direction in which the X-ray beam for the focusing method goes out from the X-ray focus and the direction in which the X-ray beam for the parallel beam method goes out of the X-ray focus is larger. When the mirror is designed for certain characteristic X-rays having the wavelength longer than CuKα rays or the multilayer period of the multilayer thin film of the mirror is planned to be smaller, the Bragg angle $\theta_M$, with which X-rays are reflected at the mirror, becomes larger. For example, assuming that the CrKα rays, whose wavelength λ is 0.229 nanometers, are used and the multilayer period d has been planned to be 1 nanometer, the angle $\theta_M$ becomes 6.57 degrees. Therefore, the angle δ, which equals to $2\theta_M$, becomes 13.14 degrees. As has been stated above in detail, if the Bragg angle becomes larger, the angle α also becomes larger, so that the changing operation from the focusing method into the parallel beam method with the X-ray tube kept stationary would cause that the X-ray take-off angle φ becomes far apart from the optimum angle. Then, in changing the focusing method shown in FIG. 6a for the parallel beam method shown in FIG. 6b, it is preferable that the X-ray tube 10 is turned around the X-ray focus 34 by the angle α in a direction 64 at the same time as the path-selection slit device 18 is turned by 180 degrees. As a result, the X-ray beam can be taken out with the take-off angle φ of about 6 degrees in the parallel beam method too. It is noted that since the X-ray tube 10 is turned around the X-ray focus 34, the position of the X-ray focus 34 would not vary even with the X-ray tube 10 rotation.

Figure 5:
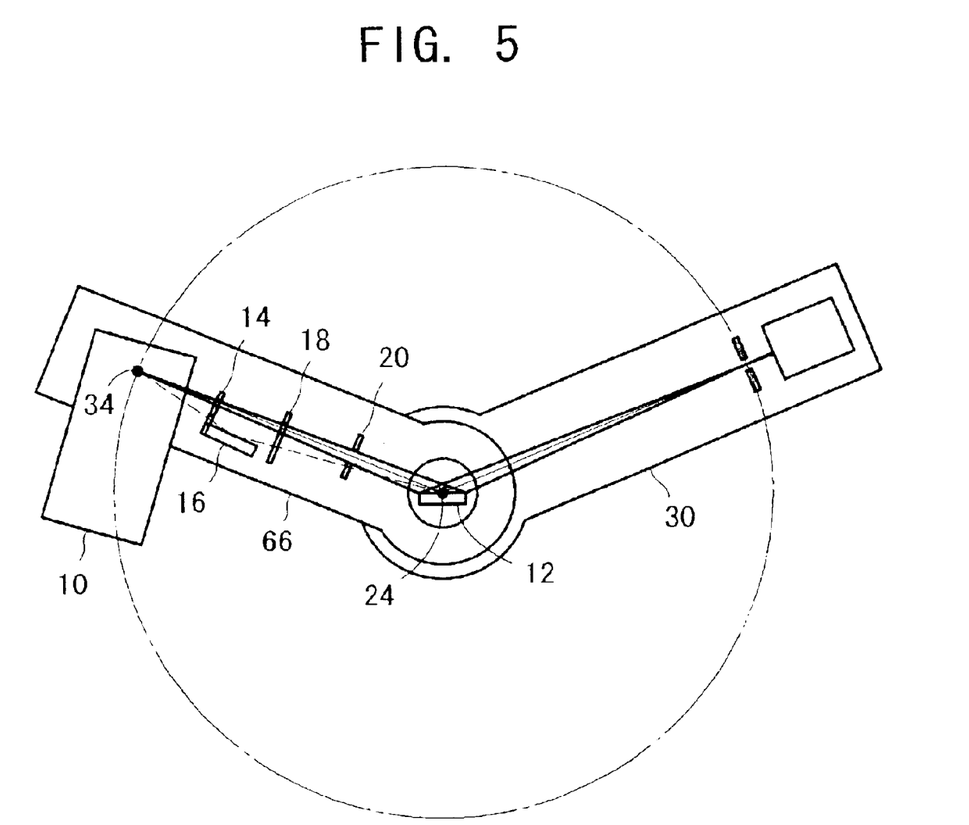
FIG. 5 is a front elevation illustrating an elementary configuration of the third embodiment of the X-ray diffraction apparatus according to the present invention.

FIG. 5 is a front elevation illustrating the third embodiment of the X-ray diffraction apparatus according to the invention. In the third embodiment, the X-ray diffraction measurement can be carried out with the sample kept in a horizontal condition. An incident optical system support 66 can turn around the axis of rotation 24 of the goniometer, whereas a detector support 30 also can turn around the axis of rotation 24 of the goniometer. In the measurement with the focusing method, the incident optical system support 66 and the detector support 30 are turned synchronously, with the sample kept stationary, in the opposite directions with the same angular speed to measure a diffraction pattern.

The incident optical system support 66 supports all of the X-ray tube 10, the multilayer mirror 16, the aperture slit plate 14, the path-selection slit device 18 and the divergence slit 20. The changing operation from the focusing method into the parallel beam method can be carried out with the same steps as explained in the first embodiment. The positional relationship among the X-ray focus 34, center of the sample 12 and the mirror 16 would not vary even after the change between the focusing method and the parallel beam method.

What is claimed is:

1. X-ray diffraction apparatus in which an X-ray source emits an X-ray beam which is incident upon a sample, diffracted by said sample and detected by an X-ray detector, comprises:

(a) a first incident path along which said X-ray beam is incident upon said sample with a predetermined divergence angle;

(b) a second incident path along which said X-ray beam is reflected by a parabolic multilayer mirror to become a parallel beam and thereafter incident upon said sample;

(c) a path-selection slit device which can open any one of said first incident path and said second incident path whereas close off the other of said first incident path and said second incident path;

(d) an X-ray source in which a position of X-ray generation does not vary independently upon selection of said first incident path or said second incident path; and (e) a sample holder in which a center position of said sample does not vary independently upon selection of said first incident path or said second incident path.

2. X-ray diffraction apparatus according to claim 1, wherein said path-selection slit device has a disc-like shape and an elongate opening which is eccentric with an axis of rotation of said path-selection slit device, and can be turned by 180 degrees to enable change between a first state which opens said first incident path whereas closes off said second incident path and a second state which closes off said first incident path whereas opens said second incident path.

3. X-ray diffraction apparatus according to claim 1, wherein an aperture slit plate is fixed to said multilayer mirror, said aperture slit plate being formed with a first aperture allowing an X-ray beam for a focusing method to pass through and a second aperture allowing an X-ray beam for a parallel beam method to pass through.

4. X-ray diffraction apparatus according to claim 1, wherein a divergence slit is disposed on said first incident path, said divergence slit being movable in a direction perpendicular to said first incident path.

5. X-ray diffraction apparatus according to claim 1, wherein said X-ray source is an X-ray tube having an X-ray focus, said X-ray tube being able to turn around said X-ray focus.

6. X-ray diffraction method in which an X-ray source emits an X-ray beam which is incident upon a sample, diffracted by said sample and detected by an X-ray detector, comprising the steps of:

(a) preparing a first incident path along which said X-ray beam is incident upon said sample with a predetermined divergence angle and a second incident path along which said X-ray beam is reflected by a parabolic multilayer mirror to become a parallel beam and thereafter incident upon said sample;

(b) opening any one of said first incident path and said second incident path whereas closing off the other of said first incident path and said second incident path under a condition that a position of X-ray generation in said X-ray source and a center of said sample do not vary;

(c) irradiating said sample with said X-ray beam via an opened one of said first incident path and said second incident path; and (d) detecting X-rays which have been diffracted by said sample.

7. X-ray diffraction method according to claim 6, wherein said X-ray source is an X-ray tube having an X-ray focus, said X-ray tube being turned around said X-ray focus to a desired turning position depending upon a use of said first path or said second incident path so that an X-ray take-off angle in said X-ray tube can be adjusted to become the same angle between a use of said first incident path and a use of said second incident path.

* * * * *